United States Patent [19]

Vértesy et al.

[11] 4,451,455

[45] May 29, 1984

[54] α-AMYLASE INACTIVATOR, A PROCESS FOR ITS PREPARATION, AN AGENT BASED ON THIS INACTIVATOR AND ITS USE

[75] Inventors: László Vértesy, Eppstein; Miroslav Mracek, Frankfurt am Main; Gerhard Braunitzer; Heinz Aschauer, both of Munich, all of Fed. Rep. of Germany

[73] Assignee: Hoechst Aktiengesellschaft, Frankfurt am Main, Fed. Rep. of Germany

[21] Appl. No.: 309,444

[22] Filed: Oct. 7, 1981

[30] Foreign Application Priority Data

Oct. 9, 1980 [DE] Fed. Rep. of Germany ....... 3038130
Feb. 26, 1981 [DE] Fed. Rep. of Germany ....... 3107106

[51] Int. Cl.$^3$ .................. A61K 37/02; C07C 103/52; C12P 21/00; C12P 21/02
[52] U.S. Cl. .............................. 424/177; 260/112.5 R; 435/68; 435/70
[58] Field of Search .................. 260/112.5 R; 435/68, 435/70

[56] References Cited

U.S. PATENT DOCUMENTS 4,226,764 10/1980 Oeding et al. ................. 435/68
4,282,318 8/1981 Oeding et al. ................. 435/68

FOREIGN PATENT DOCUMENTS 2701890 7/1978 Fed. Rep. of Germany.
1129125 2/1966 United Kingdom.

OTHER PUBLICATIONS

Aschauer et al., Hoppe-Seyler's Z. Physical. Chem., 362(4), 1981, pp. 465–467.

Primary Examiner—Delbert R. Phillips
Assistant Examiner—F. T. Moezie
Attorney, Agent, or Firm—Curtis, Morris & Safford

[57] ABSTRACT

What are disclosed are two peptides having α-amylase inactivator activity, a method for making the inhibitors, in combination, by culturing Streptomyces tendae 4158 or Streptomyces tendae HAG 1226, methods for separating the combination into its two components, and methods and compositions for treating diabetes, pre-diabetes, or adiposity by administration of such peptide α-amylase inhibitors.

9 Claims, No Drawings

α-AMYLASE INACTIVATOR, A PROCESS FOR ITS PREPARATION, AN AGENT BASED ON THIS INACTIVATOR AND ITS USE

An α-amylase inhibitor, which is obtained by the fermentation of *Streptomyces tendae* 4158 (ATCC 31210) and its variants and mutants, is described in German Offenlegungsschrift No. 2,701,890. It is a peptide with respect to its chemical structure and has the ability irreversibly to inactivate α-amylase. Owing to these properties, it can be used for regulating the blood sugar level.

It has now been found that by using an improved process for obtaining and purifying the α-amylase inactivator, also designated in the following text as HOE 467, the inactivator can be prepared in relatively high purity by relatively simple rules, and that the highly pure substance comprises two components, designated in the following text as HOE 467-A and HOE 467-B.

If not otherwise stated, α-amylase inactivator is understood, in the embodiments mentioned above and in the following text, as meaning the mixture as well as the individual components.

The invention therefore relates to an α-amylase inactivator comprising the components HOE 467-A and HOE 467-B, or comprising the component HOE 467-A or HOE 467-B, and a process for its preparation and separation into the two components.

The description of the substances given in German Offenlegungsschrift No. 2,701,890 applies to the α-amylase inactivator HOE 467 according to the invention, and to the two individual components HOE 467-A and HOE 467-B, with the exception of the following essential differences:

HOE 467 has an increased enzymatic activity and comprises the 2 components HOE 467-A and HOE 467-B, which are characterised by the following data: HOE 467-A is characterised by the following aminoacid composition:

| Asp 6 | Glu 7 | Ala 7 |       | Tyr 6 | Lys 1 |
|-------|-------|-------|-------|-------|-------|
| Thr 8 | Pro 3 | Val 8 | Ile 2 |       | Arg 3 |
| Ser 5 | Gly 7 | Cys 4 | Leu 4 | His 2 | Trp 1 |

HOE 467-B has the following aminoacid composition:

| Asp 5   | Glu 6–7 | Ala 7   |       | Tyr 6 | Lys 1 |
|---------|---------|---------|-------|-------|-------|
| Thr 6–8 | Pro 3   | Val 7–8 | Ile 2 |       | Arg 3 |
| Ser 4–5 | Gly 7   | Cys 4   | Leu 4 | His 2 | Trp 1 |

The determination of Trp was effected by absorption measurement in UV light. The remaining aminoacids were determined by hydrolytic cleavage.

The isoelectric points of the two components differ by a trivial amount and are dependent on the ionic strength and the methods of determination (Biochemisches Taschenbuch (Biochemical Handbook), edited by H. M. Rauen, Springer Verlag, 1964). The values obtained by isoelectric focusing (R. C. Allen, H. R. Maurer: Electrophoresis and Isoelectric Focusing in Polyacrylamide Gel, W. de Gruyter, Berlin, 1974) are:

HOE 467-A: 4.35±0.15
HOE 467-B: 4.53±0.15

The highly pure α-amylase inactivator HOE 467-A according to the invention also has aspartic acid as its end group, comprises 74 aminoacids with the following sequence Asp-Thr-Thr-Val-Ser-Glu-Pro-Ala-Pro-Ser-Cys-Val-Thr-Leu-Tyr-Gln-Ser-Trp-Arg-Tyr-Ser-Gln-Ala-Asp-Asn-Gly-Cys-Ala-Glu-Thr-Val-Thr-Val-Lys-Val-Val-Tyr-Glu-Asp-Asp-Thr-Glu-Gly-Leu-Cys-Tyr-Ala-Val-Ala-Pro-Gly-Gln-Ile-Thr-Thr-Val-Gly-Asp-Gly-Tyr-Ile-Gly-Ser-His Gly-His-Ala-Arg-Tyr-Leu-Ala-Arg-Cys-Leu, and has disulfide bridges between Cys 11 and Cys 27 and between Cys 45 and Cys 73. Its molecular weight is calculated on the basis of the composition to be 7958.

For determining the aminoacid composition, HOE 467-A was hydrolytically cleaved, and the corresponding acids Glu and Asp were formed from glutamine (Gln) and asparagine (Asn).

The inactivator HOE 467-B is a degradation product of HOE 467-A, shortened at the N-terminal end of the chain. Thus, for example, serine can be the terminal group in one of the possible degradation products.

For the two components HOE 467-A and HOE 467-B, the specific inhibitory action against the α-amylase from pig's pancreas is $1.7 \cdot 10^7$ AIU/g.

The inhibitory action was determined in the amylase test described below:

Amylase test

An amylase inhibitor unit (AIU) is defined as the quantity of inhibitor which is capable, under the test conditions, of a 50% inhibition of two amylase units (AU). According to international agreement, an amylase unit is the enzyme quantity which cleaves, in one minute, $1\mu$ equivalent of glucosidic bonds in starch. The $\mu$ equivalents of cleaved glucosidic bonds are determined photometrically, using dinitrosalicylic acid, as $\mu$ equivalents of reducing sugar. The data are calculated as $\mu$ moles of maltose, which are determined by means of a maltose calibration line.

The tests are carried out as follows:

α-Amylase from pig's pancreas and the solution to be tested are pre-incubated together in 1.0 ml of 20 mM phosphate buffer, pH 6.9, and 10 mM NaCl for 10–20 minutes at 37° C. The enzymatic reaction is started by the addition of 1.0 ml of soluble starch, according to Zulkowski (0.25% in the buffer indicated). After exactly 10 minutes, the reaction is stopped with 2.0 ml of dinitrosalicylic acid color reagent (according to Boehringer Mannheim: Biochemica Information II) and the mixture is heated for 5 minutes in a boiling water bath to develop the color. After the mixture has cooled, the extinction is measured at 546 nm against the blank reagent. By using various quantities of inhibitor, the 50% inhibition in comparison to the uninhibited enzyme reaction is determined graphically by plotting the probability.

In the preparation of the α-amylase inactivator according to the invention, the strain *Streptomyces tendae* 4158 (ATCC 31210) or the derived strain *Streptomyces tendae* HAG 1266 (DSM 1912) deposited in the ATCC under Registration No. 31969, is used according to the invention. The inactivator is obtained from the culture solution. The strain *Streptomyces tendae* HAG 1266 is preferably used.

Furthermore, the invention also relates to the strain *Streptomyces tendae* HAG 1266.

The new strain differs in important properties from the strain *Streptomyces tendae* ATCC 31210. The different morphological characteristics of the two strains and properties, which are also new and are important for the fermentative preparation and the isolation of the α-amylase inactivator according to the invention, such as the more rapid growth and the α-amylase inactivator production capacity which is increased by about 40%, are striking. The melamine formation, which mainfests itself in the case of Streptomyces tendae ATCC 31210 by a brown-black coloration of the culture solution and of the culture filtrate and presents certain purification problems for the working-up, was reduced to about 1/10th in the case of the new strain HAG 1266 with the aid of genetic interventions and also changed qualitatively by a shift in the color. The melanine pigments now exhibit a reddish-yellow color spectrum. The elimination of this type of melanine in the working-up is unproblematic.

The two strains which produce α-amylase inactivator are compared in the following table:

TABLE
Properties of the strains ATCC 31210 and HAG 1266

|  | ATCC 31210 | HAG 1266 |
|---|---|---|
| Color of the substrate mycelium | yellow-brown | reddish |
| Color of the sporulated aerial mycelium | gray-brown | white-yellow |
| Morphology of the spore chains | *Retinaculum apertum* (RA) | Flexibilis (F) |
| Spore morphology | spherical, slightly verrucous to smooth surface, size ∅1 μm | spherical, sharp-edged tubercles, size ∅1.3 μm |
| Melanine formation on peptone medium | positive | negative |
| Nitrate reduction | positive | positive |
| Substrate evaluation spectrum | | |
| Glucose | ++ | +++ |
| Fructose | ± | ++ |
| Saccharose | + | +++ |
| Maltose | + | + |
| Lactose | ± | − |
| Galactose | + | − |
| Rhamnose | ± | − |
| Sorbose | − | − |
| Xylose | + | − |
| Arabinose | + | ++ |
| Inositol | ++ | − |
| Mannitol | ++ | − |
| Raffinose | ± | − |
| Cellulose | − | − |

The strain *Streptomyces tendae* HAG 1266 has been deposited in the Deutschen Sammlung von Mikroorganismen (DSM) (German Collection of Microorganisms) under the registration No. DSM 1912.

The fermentation is advantageously carried out in a manner analogous to that described in German Offenlegungsschrift No. 2,701,890.

The prepared fermentation solutions of *Streptomyces tendae* ATCC 31210 and HAG 1266 contain enzymes which can reduce the active ingredient concentration considerably during the working-up. In addition, substances such as, for example, melanine can be present, which can only be separated with difficulty by the known processes.

It has now been found that the necessary separation of the inactivator from the culture solution can readily be carried out using so-called adsorption resins (German Patent Specification No. 1,274,128 and U.S. Pat. No. 3,531,963).

The process, according to the invention, for the preparation of the α-amylase inactivator comprises cultivating *Streptomyces tendae* ATCC 31210 or HAG 1266 and separating the inactivator from the culture with the aid of adsorption resins or reverse-phase chromatography, and subsequently purifying the inactivator.

Commercial resins, such as, for example, polystyrene resins, are suitable. The resin is used by bringing it into contact with the culture filtrate. The pH value of the culture liquids is adjusted to 2 to 8, preferably 4 to 6. The solid resin selectively adsorbs the inactivator HOE 467, whereas the undesired enzymes and the major part of the impurities can be removed by filtration since they remain unbound in solution. The recovery of the HOE 467 from the resin is advantageously effected either by washing with suitable aqueous buffer solutions, such as, for example, phosphate buffer, or with aqueous solutions of organic solvents, such as, for example, lower aliphatic alcohols, acetone, acetonitrile or others. The further purification of the now concentrated inactivator HOE 467 is effected according to known processes.

The separation with adsorption resins which has been described above is based on the principle of the partitioning of different polar compounds. Still further methods of partitioning can be used for the required rapid separation. Thus, partitionings in the context of reversed phase chromatography are also suitable (G. Schwendt, Chromatographische Trennmethoden (Chromatographic Separation Methods), Georg Thieme Verlag, Stuttgart, 1979), either commercial carriers or self-prepared, for example silanized, carriers being used. Finally, liquid/liquid separation processes may also be pointed out, for example using aqueous polyethylene glycol, aqueous phosphate buffer systems, as described in principle, for example, in German Offenlegungsschrift No. 2,639,129.

It has been reported in German Offenlegungsschrift No. 2,701,890 that ion exchangers, such as, for example, DEAE cellulose, are suitable for the purification of the α-amylase inactivator HOE 467. In this process, as is customary in ion exchange chromatography, pH values were selected which provide the required degree of ionization. It has now been found, surprisingly, that if purifications are carried out—contrary to the rule—in the proximity of the isoelectric point, that is to say at a low degree of ionization, HOE 467 is separated into two components. The pH range from 4.4 to 6, preferably from 4.8 to 5.3, is suitable for the separation. In this process, one component of the active ingredient is retained by the ion exchanger and can be detached from this ion exchanger only by changing the pH value or by increasing the salt concentration. This substance is called HOE 467-A. Under the conditions mentioned, the other component remains more or less unbound by the ion exchanger and can thus readily be washed from the carrier. This component is called HOE 467-B.

Although the components are produced in sufficiently pure form for pharmaceutical use, an additional purification can still be carried out.

Thus, the inactivator HOE 467-A is purified, for example, by chromatography in the presence or absence of a dissociating buffer, preferably urea (6–8 M aqueous solution), over DEAE or cation exchanger columns, such as, for example, carboxymethylcellulose columns, and is isolated by customary methods. This additional purification is carried out, for example, before the determination of the aminoacid sequence.

The α-amylase inactivator according to the invention is resistant to enzymatic degradation. Its properties are of interest with regard to its use as a medicament, particularly as a therapeutic for diabetes and prediabetes, as well as adiposity, and with regard to its use as a dietary support. When used, the individual components as well as a mixture of HOE 467-A and HOE 467-B can be employed.

The invention therefore also relates to a pharmaceutical agent containing the amylase inactivator according to the invention and to its use.

Starch containing foodstuffs and luxury consumables lead to an increase in the blood sugar in animals and man, and thereby also to an increased insulin secretion of the pancreas. Hyperglycemia arises from the cleavage of the starch in the digestive tract, under the action of amylase and maltase, to give glucose.

In diabetics, this hyperglycemia is particularly pronounced and prolonged.

In adipose subjects, the increased insulin secretion acts on the lipogenesis and reduces the lipolysis.

Alimentary hyperglycemia and hyperinsulinemia after the uptake of starch can be reduced by the amylase inactivator claimed. The action is dependent on the dose. The amylase inactivator according to the invention can therefore be employed as a therapeutic for diabetes, prediabetes and adiposity, also as a dietary support. For this purpose, an administration at mealtimes is particularly recommended. The dosage, which should be in accordance with the weight of the patient and the individual requirement, is about 10,000 to 300,000 AIU, but can also be above or below these values in cases requiring this.

The amylase inactivator according to the invention is particularly suitable for oral administration. It can be used as the pure substance and also in the form of a pharmaceutical preparation, using the customary auxiliaries and excipients, such as, for example, talc, magnesium stearate, lactose, starch or polyethylene glycol. Tablets, push-fit capsules or even granules are suitable forms for administration.

A combined use with other medicaments, such as substances which lower the blood sugar level or which lower the lipid level, can also be of advantage.

Since higher-molecular weight peptides are not resorbed as such, or are not significantly resorbed as such, from the digestive tract, no toxicologically unacceptable side effects are to be expected from the substance according to the invention. Owing to the not uncommon aminoacid composition, any proteolytic cleavage products can also be regarded as physiologically acceptable. Accordingly, no striking symptoms could be recognized in the oral administration of even higher doses of the amylase inactivator to experimental animals. Also in the case of intravenous administration to mice (1 g/kg), the inactivator according to the invention was tolerated, in a 24 hour observation period, without a recognizable toxic effect.

To test the pharmacological action of the amylase inactivator, male Wistar rats which had fasted and which had a weight of between 200 and 250 g received, in an oral administration, the inactivator according to the invention simultaneously with 2 g of starch per kg of body weight, after a blood sample for determining the starting blood sugar value had been taken immediately before. Further samples of blood were taken from the caudal vein after 15 and 30 minutes and after 1, 2, 3 and 5 hours. The blood sugar determinations were carried out in an autoanalyzer, according to the method of Hoffman (J. Biol. Chem. 120, 51 (1937)).

NZO mice have a disturbed glucose tolerance. They are therefore particularly well suited for investigations in which the blood glucose level is affected. The experimental arrangement corresponds to that for rats. The blood samples are taken from the orbital venus plexus. The blood sugar trend is monitored over a period of 3 hours.

The active ingredient is proved on NMRI mice in an analogous manner. The blood samples are also taken from the orbital venus plexus and the blood sugar trend is monitored over a period of 3 hours.

Under these experimental arrangements, the animals treated with the inactivator according to the invention showed a smaller, more protracted blood sugar increase compared to untreated animals.

EXAMPLE 1

The strain *Streptomyces tendae* HAG 1266 is inoculated on slant tubes with a nutrient medium of the following composition:
oat flakes 50 g
$H_2O$ to 1,000 ml
pH 7.2

The inoculated tube is incubated for 10 days at 28° C. and is thereafter stored at +4° C. The spores, which are readily detached from the yellowish aerial mycelium, are suspended in 10 ml of sterilized distilled water with 0.2 ml of Tween 80. $10^8$–$10^9$ spores, that is to say 1 ml of the suspension, are used for inoculating a 300 ml Erlenmeyer flask which is charged with 35 ml of sterilized nutrient solution with a pH value of 7.2 and the following composition:
1% of glucose
1% of soya flour
0.25% of NaCl The sterilization time is 45 minutes at 121° C. and 1 bar. The flask is shaken on a shaking machine at 250 rpm and at an amplitude of 3.5 cm for 40 hours at +30° C. 5 ml of this preculture, in each case, are transferred to several Erlenmeyer flasks which are charged with 50 ml of sterilized nutrient solution and have a pH value of 7.4. The composition of this main culture is as follows:

| | |
|---|---|
| soluble starch | 4% |
| soya flour | 0.4% |
| cornsteep liquor | 0.4% |
| skimmed milk powder | 0.7% |
| glucose | 1.0% |
| $(NH_4)_2HPO_4$ | 1.2% |

The sterilization time is 45 minutes at 121° C. and 1 bar. The main cultures were shaken on a shaking machine at 250 rpm and at an amplitude of 3.5 cm for 96–120 hours at 25° C. On the third, fourth and fifth day of culture, the content of α-amylase inactivator is determined according to the test instructions.

Under the test and culture conditions, the strain *Streptomyces tendae* HAG 1266 yields 1,900 AIU/ml at an end pH of 6.4.

EXAMPLE 2

The mixture is as in Example 1, but the main fermentation is carried out in a fermenter of 15 l total volume with a charge of 10 l. The following nutrient solution composition is used:

| | |
|---|---|
| starch | 4% |
| soya flour | 0.4% |
| cornsteep liquor | 0.4% |
| skimmed milk powder | 0.7% |
| glucose | 1.0% |
| (NH$_4$)$_2$HPO$_4$ | 1.2% |

After the sterilization, the pH value should be 6.8, and it is adjusted, as required, to this value using sterilized acid (2 N H$_3$PO$_4$) or alkali solution (2 N NaOH). The main stage is inoculated with 1 l, corresponding to 10%, of a preculture as described under Example 1.

The fermentation is carried out for 50 to 70 hours at 30° C. The aeration is 300 l/hour at a rate of stirring of 250 rpm and an elevated pressure of 0.3 bar.

The course of the fermentation is controlled and monitored with respect to the inhibitor activity, the degradation of carbohydrates, the development of biomass and the physical behavior of the culture solution (surface tension, viscosity, density and osmotic pressure) by taking samples.

The maximum inhibitor activity is reached from the 60th hour of culture, with an average value of 1,800 AIU/ml. The content of the fermenter is then fed to the working-up process.

EXAMPLE 3

6.5 l of culture filtrate, obtained by filtering off under suction the Streptomyces culture obtained according to Example 2, were adjusted to pH 4.9, while stirring, with glacial acetic acid, and the mixture was introduced onto a prepared glass column. The column contained 230 g of polystyrene adsorption resin (for example Diaion ® HP 20) suspended in water. The dimensions of the column were 22×5 cm, corresponding to a volume of 430 ml. The throughput of liquid was regulated so that 6.5 l had run through after 2 hours. The adsorption process had then ended and the resin could first be washed with pure water and then eluted with water to which increasing quantities of isopropanol had been added. The liquid flowing through the column was collected in fractions of 1 l each, and was tested with respect to the enzyme-inhibiting action. The active fractions were collected and were concentrated to 100 ml by distillation in vacuo. The concentrate contained 110,000 AIU/ml.

The solution thus formed, which was now stable to salt, was directly introduced onto a DEAE ion exchanger column prepared with 1/30 phosphate buffer of pH 7.5, and was purified according to German Auslegeschrift No. 2,701,890, Example 5. 4 g of substance with 2,500 AIU/mg resulted.

EXAMPLE 4

For further purification, a glass column with a diameter of 2 cm and a height of 22 cm, corresponding to a capacity of 70 ml, was filled with DEAE cellulose which had previously been equilibrated with 1/10 M sodium acetate buffer of pH 4.9 and 0.02% of sodium azide. The substance obtained according to Example 3 was now dissolved in 10 ml of the same buffer and was introduced onto the column. The column content was first washed with 100 ml of acetate buffer, and sodium chloride was then gradually mixed with this eluting agent at such a rate that a continuous gradient was ensured. When the column throughput was collected in fractions, HOE 467-B occurred in the first fractions which were still free of sodium chloride, while the HOE 467-A component could be detected in the fractions in which the NaCl concentration was 0.25 to 0.3 molar. The fractions containing the B component and the fractions containing the A component were collected separately, dialyzed against distilled water and freeze-dried. The colorless substances each had an activity of $1.7 \cdot 10^4$ AIU/mg.

The aminoacid analysis of the products, after hydrolysis with hydrochloric acid for 20 hours, gave the following percentage compositions, with the aid of a Beckman Multichro analyzer:

| | HOE 467-A | HOE 467-B |
|---|---|---|
| Aspartic acid | 8.51 | 7.90 |
| Threonine | 10.07 | 8.17 |
| Serine | 5.41 | 5.98 |
| Glutamic acid | 11.30 | 12.39 |
| Proline | 3.28 | 3.39 |
| Glycine | 5.61 | 6.19 |
| Alanine | 6.85 | 7.41 |
| Cysteine | 4.68 | 3.83 |
| Valine | 8.69 | 8.54 |
| Methionine | — | — |
| Isoleucine | 2.93 | 3.28 |
| Leucine | 5.91 | 6.61 |
| Tyrosine | 11.28 | 12.69 |
| Phenylalanine | — | — |
| Histidine | 3.49 | 3.72 |
| Lysine | 1.78 | 2.05 |
| Arginine | 6.12 | 6.52 |

EXAMPLE 5

The α-amylase inactivators HOE 467-A and HOE 467-B are obtained from a culture solution of *Streptomyces tendae* ATCC 31210 in an analogous manner.

EXAMPLE 6

(a) Preparation of the α-amylase inactivator HOE 467-A being uniform at the N-terminal end:

HOE 467-A obtained according to Example 4 or 5 is purified by chromatography over a DEAE or carboxymethylcellulose column in the presence of aqueous 8 M urea solution as the dissociating buffer, and is isolated according to customary methods.

(b) Preparation of tryptic peptides:

The α-amylase inactivator HOE 467-A which is obtained according to (a) and which has a pure end group is either oxidized with performic acid or reacted with ethyleneimine to cleave the disulfide bridges (see C. H. W. Hirs, J. Biol. Chem. 219, 611–621 (1956) and M. A. Raftery and R. D. Cole, J. Biol. Chem. 241, 3457–3461 (1966)), and tryptic cleavage is carried out according to customary methods. The tryptic hydrolysis products are chromatographically separated and purified.

(c) Sequence analysis:

The sequence analysis was carried out according to the film technique (P. Edmann and G. Begg, Eur. J. Biochem. 1, 80–91 (1967)), using the following program:

(α) Quadrol program: The α-amylase inactivator HOE 467-A reacted according to (b) with ethyleneimine, and an activator A which had been subjected to a limited tryptic cleavage were degraded.

(β) Propyne program: The remaining peptides were degraded in this process (see G. Braunitzer and B. Schrank, Hoppe-Seyler's Z. Physiol. Chem. 351, 88

(1970) and G. Braunitzer, A. Stangel and O. Scheithauser, Hoppe-Seyler's Z. Physiol. Chem. 359, 137–146 (1978)).

(d) Aminoacid analysis:

The analysis was carried out by hydrolysis, using 6 N hydrochloric acid, of the inactivator obtained according to (a).

(e) Determination of the disulfide bridges:

For this purpose, the substance obtained according to (a) was treated, in dilute formic acid, with pepsin during the course of 18 hours, and the cleavage products were purified according to customary methods.

On the basis of the operations carried out, it was found that the substance obtained according to (a) comprises 74 aminoacids, the sequence of which is as follows: Asp-Thr-Thr-Val-Ser-Glu-Pro-Ala-Pro-Ser-Cys-Val-Thr-Leu-Tyr-Gln-Ser-Trp-Arg-Tyr-Ser-Gln-Ala-Asp-Asn-Gly-Cys-Ala-Glu-Thr-Val-Thr-Val-Lys-Val-Val-Tyr-Glu-Asp-Asp-Thr-Glu-Gly-Leu-Cys-Tyr-Ala-Val-Ala-Pro-Gly-Gln-Ile-Thr-Thr-Val-Gly-Asp-Gly-Tyr-Ile-Gly-Ser-His Gly-His-Ala-Arg-Tyr-Leu-Ala-Arg-Cys-Leu, and has disulfide bridges at the positions mentioned.

We claim:

1. An α-amylase inactivator which is a member selected from the group consisting of (1) a first peptide, HOE 467-A, having a molecular weight of 7958, an isoelectric point of 4.35±0.15, the following amino acid composition

| Asp 6 | Glu 7 | Ala 7 |       | Tyr 6 | Lys 1 |
|-------|-------|-------|-------|-------|-------|
| Thr 8 | Pro 3 | Val 8 | Ile 2 |       | Arg 3 |
| Ser 5 | Gly 7 | Cys 4 | Leu 4 | His 2 | Trp 1 | and the following amino acid sequence having a disulfide bridge between Cys 11 and Cys 27 and between Cys 45 and Cys 73: Asp-Thr-Thr-Val-Ser-Glu-Pro-Ala-Pro-Ser-Cys-Val-Thr-Leu-Tyr-Gln-Ser-Trp-Arg-Tyr-Ser-Gln-Ala-Asp-Asn-Gly-Cys-Ala-Glu-Thr-Val-Thr-Val-Lys-Val-Val-Tyr-Glu-Asp-Asp-Thr-Glu-Gly-Leu-Cys-Tyr-Ala-Val-Ala-Pro-Gly-Gln-Ile-Thr-Thr-Val-Gly-Asp-Gly-Tyr-Ile-Gly-Ser-His Gly-His-Ala-Arg-Tyr-Leu-Ala-Arg-Cys-Leu, and a second peptide, HOE 467-B, which is a degradation product of said first peptide, said degradation shortening the N-terminal end of said first peptide to produce said second peptide, said degradation product having an isoelectric point of 4.53±0.15 and the following amino acid composition

| Asp 5 | Glu 6–7 | Ala 7   |       | Tyr 6 | Lys 1 |
|-------|---------|---------|-------|-------|-------|
| Thr 6–8 | Pro 3 | Val 7–8 | Ile 2 |       | Arg 3 |
| Ser 4–5 | Gly 7 | Cys 4   | Leu 4 | His 2 | Trp 1 | and comprising six components respectively of the following amino acid sequences each having disulfide bridges as noted:

(a) Thr-Thr-Val-Ser-Glu-Pro-Ala-Pro-Ser-Cys-Val-Thr-Leu-Tyr-Gln-Ser-Trp-Arg-Tyr-Ser-Gln-Ala-Asp-Asn-Gly-Cys-Ala-Glu-Thr-Val-Thr-Val-Lys-Val-Val-Tyr-Glu-Asp-Asp-Thr-Glu-Gly-Leu-Cys-Tyr-Ala-Val-Ala-Pro-Gly-Gln-Ile-Thr-Thr-Val-Gly-Asp-Gly-Tyr-Ile-Gly-Ser-His-Gly His-Ala-Arg-Tyr-Leu-Ala-Arg-Cys-Leu, with a disulfide bridge between Cys 10 and Cys 26 and between Cys 44 and Cys 72;

(b) Thr-Val-Ser-Glu-Pro-Ala-Pro-Ser-Cys-Val-Thr-Leu-Tyr-Gln-Ser-Trp-Arg-Tyr-Ser-Gln-Ala-Asp-Asn-Gly-Cys-Ala-Glu-Thr-Val-Thr-Val-Lys-Val-Val-Tyr-Glu-Asp-Asp-Thr-Glu-Gly-Leu-Cys-Tyr-Ala-Val-Ala-Pro-Gly-Gln-Ile-Thr-Thr-Val-Gly-Asp-Gly-Tyr-Ile-Gly-Ser-His-Gly-His Ala-Arg-Tyr-Leu-Ala-Arg-Cys-Leu, with a disulfide bridge between Cys 9 and Cys 25 and between Cys 43 and Cys 71;

(c) Val-Ser-Glu-Pro-Ala-Pro-Ser-Cys-Val-Thr-Leu-Tyr-Gln-Ser-Trp-Arg-Tyr-Ser-Gln-Ala-Asp-Asn-Gly-Cys-Ala-Glu-Thr-Val-Thr-Val-Lys-Val-Val-Tyr-Glu-Asp-Asp-Thr-Glu-Gly-Leu-Cys-Tyr-Ala-Val-Ala-Pro-Gly-Gln-Ile-Thr-Thr-Val-Gly-Asp-Gly-Tyr-Ile-Gly-Ser-His-Gly-His-Ala Arg-Tyr-Leu-Ala-Arg-Cys-Leu, with a disulfide bridge between Cys 8 and Cys 24 and between Cys 42 and Cys 70;

(d) Ser-Glu-Pro-Ala-Pro-Ser-Cys-Val-Thr-Leu-Tyr-Gln-Ser-Trp-Arg-Tyr-Ser-Gln-Ala-Asp-Asn-Gly-Cys-Ala-Glu-Thr-Val-Thr-Val-Lys-Val-Val-Tyr-Glu-Asp-Asp-Thr-Glu-Gly-Leu-Cys-Tyr-Ala-Val-Ala-Pro-Gly-Gln-ILe-Thr-Thr-Val-Gly-Asp-Gly-Tyr-Ile-Gly-Ser-His-Gly-His-Ala-Arg Tyr-Leu-Ala-Arg-Cys-Leu, with a disulfide bridge between Cys 7 and Cys 23 and between Cys 41 and Cys 69;

(e) Glu-Pro-Ala-Pro-Ser-Cys-Val-Thr-Leu-Tyr-Gln-Ser-Trp-Arg-Tyr-Ser-Gln-Ala-Asp-Asn-Gly-Cys-Ala-Glu-Thr-Val-Thr-Val-Lys-Val-Val-Tyr-Glu-Asp-Asp-Thr-Glu-Gly-Leu-Cys-Tyr-Ala-Val-Ala-Pro-Gly-Gln-Ile-Thr-Thr-Val-Gly-Asp-Gly-Tyr-Ile-Gly-Ser-His-Gly-His-Ala-Arg-Tyr Leu-Ala-Arg-Cys-Leu, with a disulfide bridge between Cys 6 and Cys 22 and between Cys 40 and Cys 68; and (f) Pro-Ala-Pro-Ser-Cys-Val-Thr-Leu-Tyr-Gln-Ser-Trp-Arg-Tyr-Ser-Gln-Ala-Asp-Asn-Gly-Cys-Ala-Glu-Thr-Val-Thr-Val-Lys-Val-Val-Tyr-Glu-Asp-Asp-Thr-Glu-Gly-Leu-Cys-Tyr-Ala-Val-Ala-Pro-Gly-Gln-Ile-Thr-Thr-Val-Gly-Asp-Gly-Tyr-Ile-Gly-Ser-His-Gly-His-Ala-Arg-Tyr-Leu Ala-Arg-Cys-Leu, with a disulfide bridge between Cys 5 and Cys 21 and between Cys 39 and Cys 67.

2. An α-amylase inactivator as in claim 1 which is HOE 467-A.

3. An α-amylase inactivator as in claim 1 which is HOE 467-B.

4. A method for making an α-amylase inactivator comprising said first and second peptides of claim 1, in combination, which method comprises cultivating *Streptomyces tendae* HAG 1266.

5. A method for making an α-amylase activator as in claim 1 which method comprises cultivating *Streptomyces tendae* ATCC 31210 or *Streptomyces tendae* HAG 1266, separating the inactivators, in combination, from the culture with an adsorption resin or by reversed phase chromatography, and then further separating the combined inactivators by treating with an ion exchanger in a pH range from 4.4 to 6, whereby said first peptide, HOE 476-A is selectively retained on said ion exchanger.

6. *Streptomyces tendae* HAG 1266.

7. A pharmaceutical preparation for the treatment of diabetes, pre-diabetes, or adiposity, which preparation comprises an effective amount of an α-amylase inactivator as in claim 1 and a pharmaceutically acceptable carrier therefor.

8. A method for treating diabetes, pre-diabetes, or adiposity in a patient suffering therefrom, which method comprises orally administering to said patient an effective amount of an α-amylase inactivator as in claim 1.

9. A method as in claim 5 wherein said HOE 476-A is recovered from said ion exchanger and is further purified and isolated by chromatography on a DEAE-cellulose or carboxymethyl cellulose column in the presence of a 6–8 molar aqueous solution of urea.

* * * * *

UNITED STATES PATENT AND TRADEMARK OFFICE
CERTIFICATE OF CORRECTION

PATENT NO.    :  4,451,455
DATED         :  May 29, 1984
INVENTOR(S)   :  Vertesy et al.

It is certified that error appears in the above-identified patent and that said Letters Patent is hereby corrected as shown below:

Column 2, line 8, change "His Gly" to --His-Gly--.

Column 9, line 24, change "His Gly" to --His-Gly--.

Claim 1, line 18 (column 9, line 46), change "His Gly" to --His-Gly--;
       line 38 (column 9, line 67), change "Gly His" to --Gly-His--;
       line 47 (column 10, line 8), change "His Ala" to --His-Ala--;
       line 56 (column 10, line 17), change "Ala Arg" to --Ala-Arg--;
       line 65 (column 10, line 26), change "Arg Tyr" to --Arg-Tyr--;
       line 73 (column 10, line 34), change "Tyr Leu" to --Tyr-Leu--;
       line 81 (column 10, line 42), change "Leu Ala" to --Leu-Ala--.

Signed and Sealed this

Twenty-first Day of May 1985

[SEAL]

Attest:

DONALD J. QUIGG

Attesting Officer    Acting Commissioner of Patents and Trademarks